(12) United States Patent
Sato et al.

(10) Patent No.: US 7,670,303 B2
(45) Date of Patent: Mar. 2, 2010

(54) BODY MOTION MEASURING APPARATUS

(75) Inventors: Tomio Sato, Hiraka-machi (JP); Kenji Nishibayashi, Tokyo (JP)

(73) Assignee: Tanita Corporation, Tokyo (JP)

( * ) Notice: Subject to any disclaimer, the term of this patent is extended or adjusted under 35 U.S.C. 154(b) by 989 days.

(21) Appl. No.: 10/978,354

(22) Filed: Nov. 2, 2004

(65) Prior Publication Data
US 2005/0096569 A1    May 5, 2005

(30) Foreign Application Priority Data
Nov. 4, 2003    (JP) .............. 2003-374495

(51) Int. Cl.
*A61B 5/103* (2006.01)
*A61B 5/117* (2006.01)
*G01C 21/00* (2006.01)
*G01C 22/00* (2006.01)

(52) U.S. Cl. ............. 600/595; 377/24.2; 702/160

(58) Field of Classification Search ......... 600/595; 377/24.2; 702/160
See application file for complete search history.

(56) References Cited

U.S. PATENT DOCUMENTS 5,446,775 A * 8/1995 Wright et al. .......... 377/24.2
5,724,265 A * 3/1998 Hutchings .............. 702/141
2002/0089425 A1* 7/2002 Kubo et al. ............. 340/573.1

FOREIGN PATENT DOCUMENTS

| JP | 9-223214 | 8/1997 |
| JP | 2002-191580 | 7/2002 |

* cited by examiner

*Primary Examiner*—Max Hindenburg
*Assistant Examiner*—Emily M Lloyd
(74) *Attorney, Agent, or Firm*—McDermott Will & Emery LLP

(57) ABSTRACT

A body motion measuring apparatus is described, embodiments of which include an apparatus for detecting the magnitudes of motions in different directions at a time using body motion sensors, calculating the size V of a composite vector based on the relationship between the magnitudes of the motions, comparing the size V of the composite vector with a reference value to determine whether the size V of the composite vector is adequate, calculating an angle θ based on the relationship between the magnitudes of the motions when V is determined to be adequate, calculating a body motion output M taking the angle θ into account, and counting a predetermined body motion based on the relationship between M and a predetermined elapsed time.

12 Claims, 15 Drawing Sheets

BODY MOTION MEASURING APPARATUS

BACKGROUND OF THE INVENTION (i) Field of the Invention

The present invention relates to a body motion measuring apparatus which can be worn or carried freely and can measure a predetermined body motion (e.g., walking).

(ii) Description of the Related Art

In recent years, a pedometer is provided that can always detect a vibrational component in a vertical direction even if the direction of the device held is changed when a user who carries it in a pocket or a bag or on a waist belt changes his position.

Heretofore, such a pedometer has such techniques as disclosed in Patent Publications 1 and 2.

To brief the techniques, a pedometer in Patent Publication 1 comprises a plurality of acceleration sensors differing from one another in detection directions and an angle detection sensor in a main unit, detects the direction (angle) of the main unit by the angle detection sensor, selects an acceleration sensor capable of detection at the direction (angle) of the main unit from the plurality of acceleration sensors, and counts steps based on a detection signal from the selected acceleration sensor.

Meanwhile, a body motion detection device in Patent Publication 2 comprises a plurality of acceleration sensors (body motion sensors) differing from each other in detection directions in a main unit, performs the waveform processings of the acceleration sensors, selects one of the acceleration sensors if the number of acceleration waveforms obtained from output signals of the one of the acceleration sensors stored in a buffer 1 is equal to or larger than the number of acceleration waveforms obtained from output signals of the one of the acceleration sensors stored in a buffer 2 after passage of a predetermined time period or, if not, selects the other acceleration sensor, and counts steps based on a detection signal from the selected acceleration sensor.

Patent Publication 1

Japanese Patent Laid-Open Publication No. 9-223214

Patent Publication 2

Japanese Patent Laid-Open Publication No. 2002-191580

However, the above pedometer in Patent Publication 1 has a problem that use of the angle detection sensor causes high costs. Meanwhile, the above body motion detection device in Patent Publication 2 has a problem that when the direction of the body motion detection device held changes, a detection output from the acceleration sensor changes according to the angle at which the device has been inclined as exemplified by the relationship between angles and detection outputs as represented by the graph shown in FIG. 15, so that the detection output is not determined to be a value to be counted as a step by subsequent steps, resulting in an error in the number of counted steps.

Thus, an object of the present invention is to solve the above problems of the prior art and provide a body motion measuring apparatus which measures a predetermined body motion at low costs and with reduced errors.

SUMMARY OF THE INVENTION

A body motion measuring apparatus of the present invention comprises:
body motion sensors,
composite vector calculation means,
composite vector determination means,
angle calculation means, body motion output calculation means, and
body motion counting means, wherein
the body motion sensors detect the magnitudes of motions in different directions at a time,
the composite vector calculation means calculates the size of a composite vector derived based on the relationship between the magnitudes of the motions in the directions detected by the body motion sensors,
the composite vector determination means determines the adequacy of the size of the composite vector calculated by the composite vector calculation means,
the angle calculation means calculates an angle derived based on the relationship between the magnitudes of the motions in the directions detected by the body motion sensors, when the size of the composite vector determined by the composite vector determination means is adequate,
the body motion output calculation means calculates a body motion output derived from the relationship between the magnitudes of the motions in the directions detected by the body motion sensors and the angle by the angle calculation means, and
the body motion counting means times predetermined elapsed time and counts a predetermined body motion based on the relationship between the body motion output calculated by the body motion output calculation means and the predetermined elapsed time.

Further, the body motion sensors detect the magnitudes X and Y of motions in X and Y directions perpendicular to each other at a time,
the composite vector calculation means calculates the size V of a composite vector by substituting the magnitudes X and Y of the motions in the directions perpendicular to each other into a formula represented by $V=\sqrt{(X^2+Y^2)}$,
the composite vector determination means compares the size V of the composite vector calculated by the composite vector calculation means with a reference value to determine whether the size V is not smaller than the reference value,
the angle calculation means calculates an angle $\theta$ by substituting the magnitudes X and Y of the motions in the directions perpendicular to each other detected at a time by the body motion sensors into a formula represented by $\theta=\tan^{-1}(Y/X)$, and
the body motion output calculation means calculates a body motion output M by substituting the magnitudes X and Y of the motions in the directions perpendicular to each other detected at a time by the body motion sensors and the angle $\theta$ calculated by the angle calculation means into a formula represented by $M=X\cos\theta+Y\sin\theta$.

Further, the body motion sensors detect the magnitudes X, Y and Z of motions in X, Y and Z directions perpendicular to one another at a time,
the composite vector calculation means calculates the size V of a composite vector by substituting the magnitudes X, Y and Z of the motions in the directions perpendicular to one another detected at a time by the body motion sensors into a formula represented by $V=\sqrt{(X^2+Y^2+Z^2)}$,
the composite vector determination means compares the size V of the composite vector calculated by the composite vector calculation means with a reference value to determine whether the size V is not smaller than the reference value,
the angle calculation means calculates an angle $\theta_{XY}$ by substituting the magnitudes X and Y of the motions in the directions perpendicular to each other detected at a time by the body motion sensors into a formula represented by $\theta_{XY}=\tan^{-1}(Y/X)$, the body motion output calculation means calculates a body motion output B based on the magnitudes Y and X of the motions in the directions perpendicular to each other, by substituting X and Y out of the magnitudes of the motions in the directions perpendicular to one another detected at a time by the body motion sensors and the angle $\theta_{XY}$ calculated by the angle calculation means into a formula represented by $B=X\cos\theta_{XY}+Y\sin\theta_{XY}$, the angle calculation means also calculates an angle $\theta_{BZ}$ by substituting Z out of the magnitudes of the motions in the directions perpendicular to one another detected at a time by the body motion sensors and the body motion output B calculated by the body motion output calculation means into a formula represented by $\theta_{BZ}=\tan^{-1}(Z/B)$, and the body motion output calculation means also calculates a body motion output M based on the magnitudes X, Y and Z of the motions in the directions perpendicular to one another, by substituting the calculated body motion output B, Z out of the magnitudes of the motions in the directions perpendicular to one another detected at a time by the body motion sensors, and the angle $\theta_{BZ}$ calculated by the angle calculation means into a formula represented by $M=B\cos\theta_{BZ}+Z\sin\theta_{BZ}$.

Further, the body motion counting means counts the body motion as the predetermined body motion when the body motion output M calculated by the body motion output calculation means is larger than an upper limit.

Further, the body motion counting means counts the body motion as the predetermined body motion when the body motion output M calculated by the body motion output calculation means is larger than an upper limit and lower than a lower limit.

Further, the body motion counting means counts the body motion as the predetermined body motion based on the relationship between the state of change in difference between the upper peak and lower peak of the body motion output M calculated by the body motion output calculation means and the predetermined elapsed time.

The body motion measuring apparatus of the present invention determines a body motion output by calculating a composite vector from the magnitudes of motions in different directions by taking into account an angle from the magnitudes of the motions in the different directions detected by the body motion sensors. Hence, the same body motion output, i.e., a body motion output with a small degree of measurement errors can be obtained at low costs, regardless of what angle the body motion measuring apparatus is inclined at.

DETAILED DESCRIPTION OF THE PREFERRED EMBODIMENTS

Figure 1:
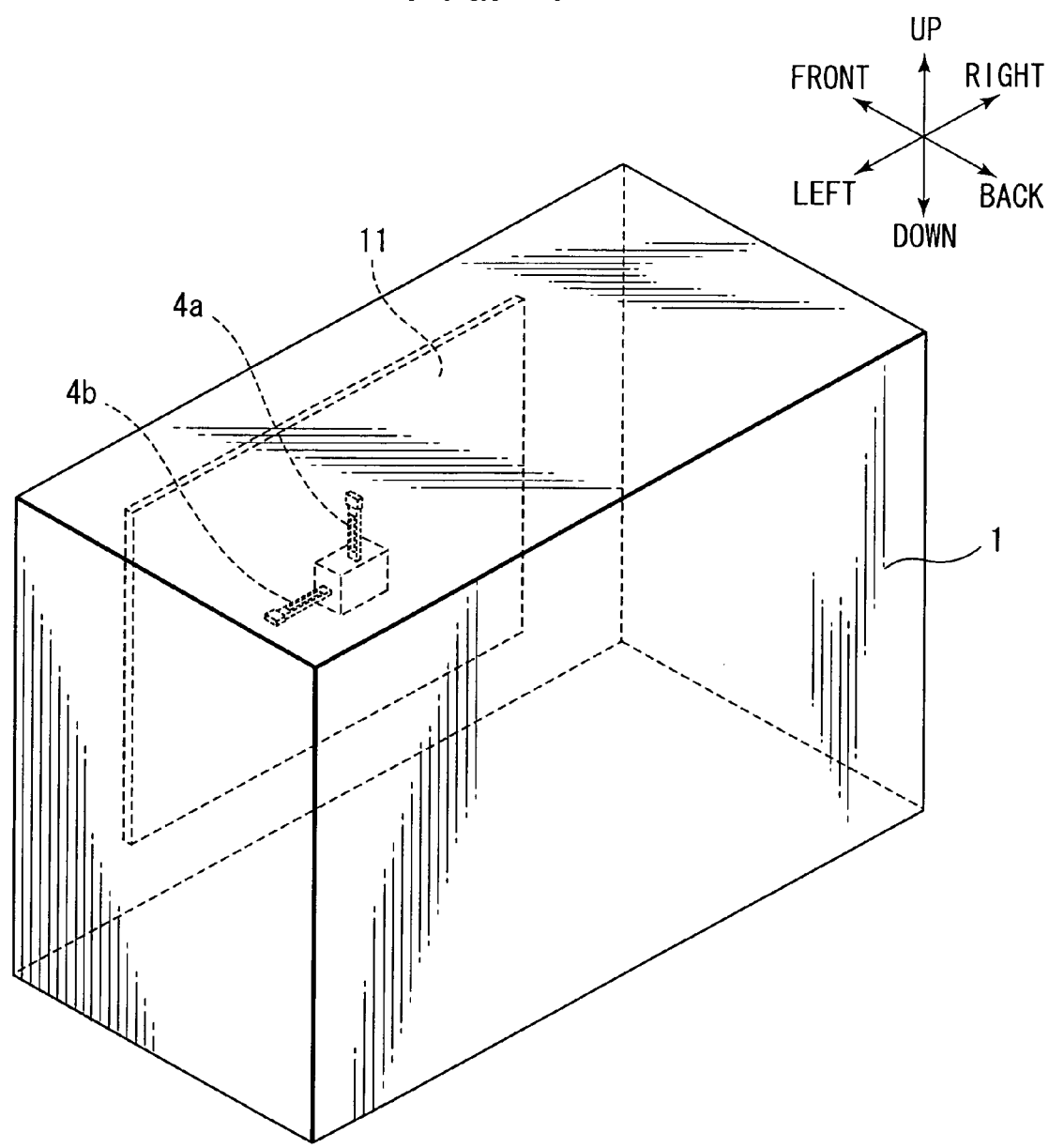
FIG. 1 is a perspective view of a body motion measuring apparatus (Example 1).

The present invention has achieved the object of measuring a predetermined body motion at low costs and with reduced measurement errors by the following constitution that data on inclination when a body motion measuring apparatus is held is obtained based on detection data from body motion sensors (acceleration sensors) and a body motion output is obtained by combining the subsequent detection data from the body motion sensors with the inclination data.

A body motion measuring apparatus of the present invention comprises:

body motion sensors,
composite vector calculation means,
composite vector determination means, angle calculation means,
body motion output calculation means, and
body motion counting means, wherein the body motion sensors detect the magnitudes of motions in different directions at a time, the composite vector calculation means calculates a composite vector derived based on the relationship between the magnitudes of the motions in the directions detected by the body motion sensors, the composite vector determination means determines the adequacy of the size of the composite vector calculated by the composite vector calculation means, the angle calculation means calculates an angle derived based on the relationship between the magnitudes of the motions in the directions detected by the body motion sensors, when the size of the composite vector determined by the composite vector determination means is adequate, the body motion output calculation means calculates a body motion output derived from the relationship between the magnitudes of the motions in the directions detected by the body motion sensors and the angle by the angle calculation means, and the body motion counting means times predetermined elapsed time and counts a predetermined body motion based on the relationship between the body motion output calculated by the body motion output calculation means and the elapsed time.

Hereinafter, the present invention will be described in detail by use of the drawings.

EXAMPLE 1

Firstly, the constitution of a body motion measuring apparatus (embodiment for preventing the influence of measurement error by inclination in two axial directions) as Example 1 will be described by use of a perspective view of the body motion measuring apparatus in FIG. 1 and a block diagram in FIG. 2 for illustrating the constitution of the body motion measuring apparatus.

The body motion measuring apparatus as Example 1 has an input unit 2 and a display unit 3 on the front face of chassis 1 and also has an electronic substrate 11 inside the chassis 1. The electronic substrate 11 comprises body motion sensors 4 (4a for an X axis and 4b for a Y axis), amplifiers 5 and 6, AD converters 7 and 8, a storage unit 9 and a CPU 10. These components roughly constitute the whole apparatus.

The input unit 2 takes inputs for starting measurements, switching, setting/registration, and the like. The display unit 3 displays an input status, measurement results, and the like. The storage unit 9 stores various data.

Figure 2:
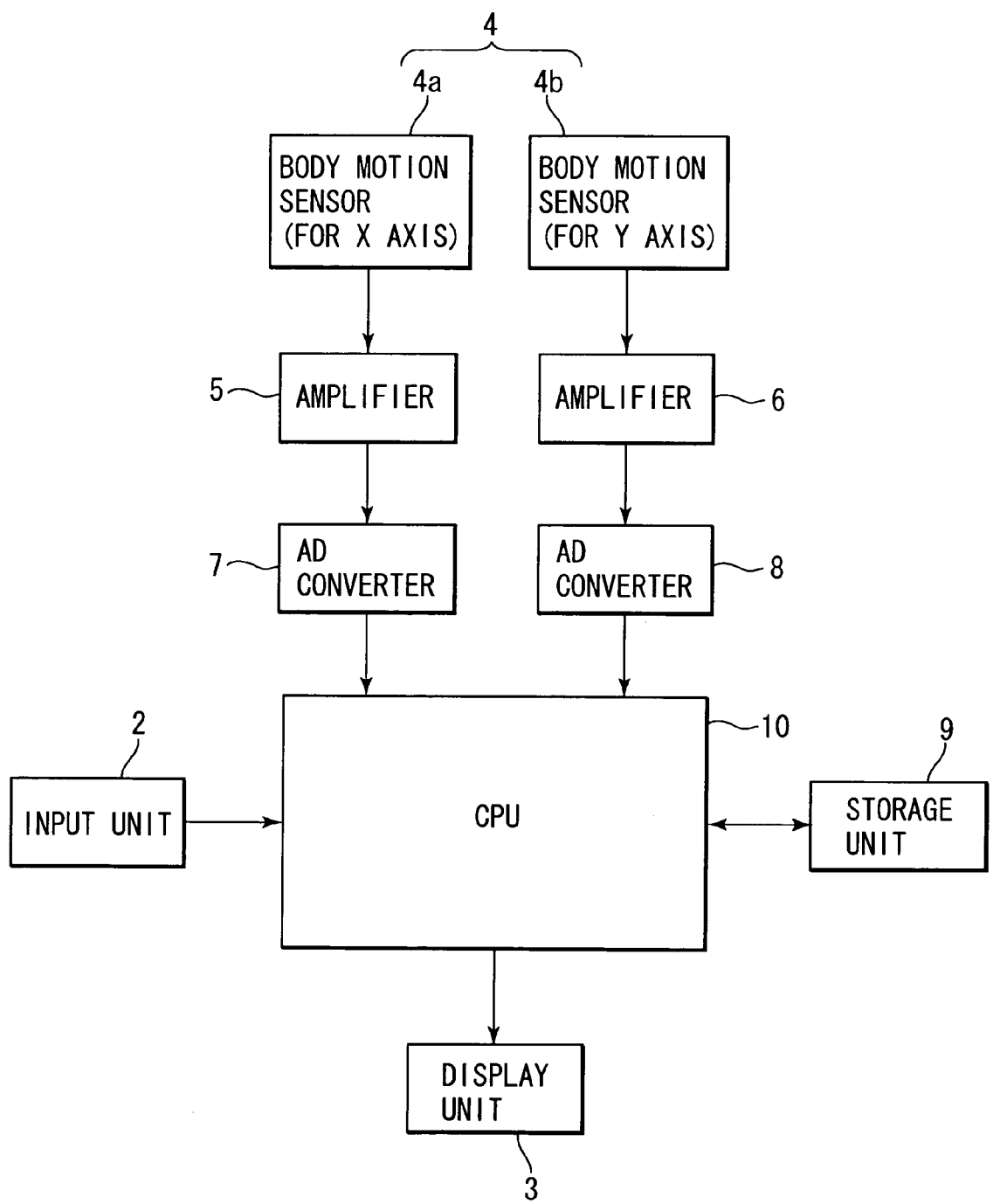
FIG. 2 is a block diagram showing the constitution of the body motion measuring apparatus (Example 1).

The body motion sensor (for the X axis) 4a detects the magnitude of a motion of the chassis 1 in its left or right direction, when the direction of the chassis 1 is defined as shown in FIG. 1 with respect to the directions (front, back, up, down, left and right). The body motion sensor (for the Y axis) 4b detects the magnitude of a motion of the chassis 1 in its up or down direction, when the direction of the chassis 1 is defined as shown in FIG. 1 with respect to the directions (front, back, up, down, left and right). The body motion sensor (for the X axis) 4a and the body motion sensor (for the Y axis) 4b detect body motions at a time (simultaneously).

The amplifier 5 amplifies an output (analog) from the body motion sensor (for the X axis) 4a. The amplifier 6 amplifies an output from the body motion sensor (for the Y axis) 4b. The AD converter 7 digitizes an output (analog) from the amplifier 5. The AD converter 8 digitizes an output (analog) from the amplifier 6.

The CPU 10 comprises composite vector calculation means, composite vector determination means, angle calculation means, body motion output calculation means and body motion counting means and calculates various data.

The composite vector calculation means calculates a composite vector derived based on the relationship between the magnitude of a motion in the direction detected by the body motion sensor (for the X axis) 4a and the magnitude of a motion in the direction detected by the body motion sensor (for the Y axis) 4b. More specifically, the composite vector calculation means calculates the size of a composite vector V by substituting an output X from the AD converter 7 based on the body motion sensor (for the X axis) 4a and an output Y from the AD converter 8 based on the body motion sensor (for the Y axis) 4b into the following formula (1).

$$V=\sqrt{(X^2+Y^2)} \tag{1}$$

The composite vector determination means determines whether the size of the composite vector calculated by the composite vector calculation means is adequate or not. More specifically, the composite vector determination means compares the size of the composite vector calculated by the composite vector calculation means with a reference value so as to determine whether the size of the vector is not smaller than the reference value. The reference value is a value representing a size which can be a candidate for the size of a composite vector by a predetermined body motion.

The angle calculation means calculates an angle derived based on the relationship between the magnitude of the motion in the direction detected by the body motion sensor (for the X axis) 4a and the magnitude of the motion in the direction detected by the body motion sensor (for the Y axis) 4b. More specifically, the angle calculation means calculates an angle θ by substituting the output X from the AD converter 7 based on the body motion sensor (for the X axis) 4a and the output Y from the AD converter 8 based on the body motion sensor (for the Y axis) 4b into the following formula (2).

$$\theta=\tan^{-1}(Y/X) \tag{2}$$

The body motion output calculation means calculates a body motion output derived based on the relationship between the magnitudes X and Y of the motions in the directions detected by the body motion sensor (for the X axis) 4a and the body motion sensor (for the Y axis) 4b and the angle calculated by the angle calculation means. More specifically, the body motion output calculation means calculates a body motion output M by substituting the output X from the AD converter 7 based on the body motion sensor (for the X axis) 4a, the output Y from the AD converter 8 based on the body motion sensor (for the Y axis) 4b, and the angle θ calculated by the angle calculation means into the following formula (3).

$$M=X\cos\theta+Y\sin\theta \tag{3}$$

The body motion counting means times predetermined elapsed time and counts a predetermined body motion based on the relationship between the body motion output calculated by the body motion output calculation means and the predetermined elapsed time. More specifically, the body motion counting means compares the body motion output calculated by the body motion output calculation means with an upper limit so as to determine whether the body motion output is larger than the upper limit. When the body motion output is larger than the upper limit, the body motion counting means counts a predetermined body motion, while when the body motion output is not larger than the upper limit, the body motion counting means executes processing corresponding to the elapsed time.

Figure 3:
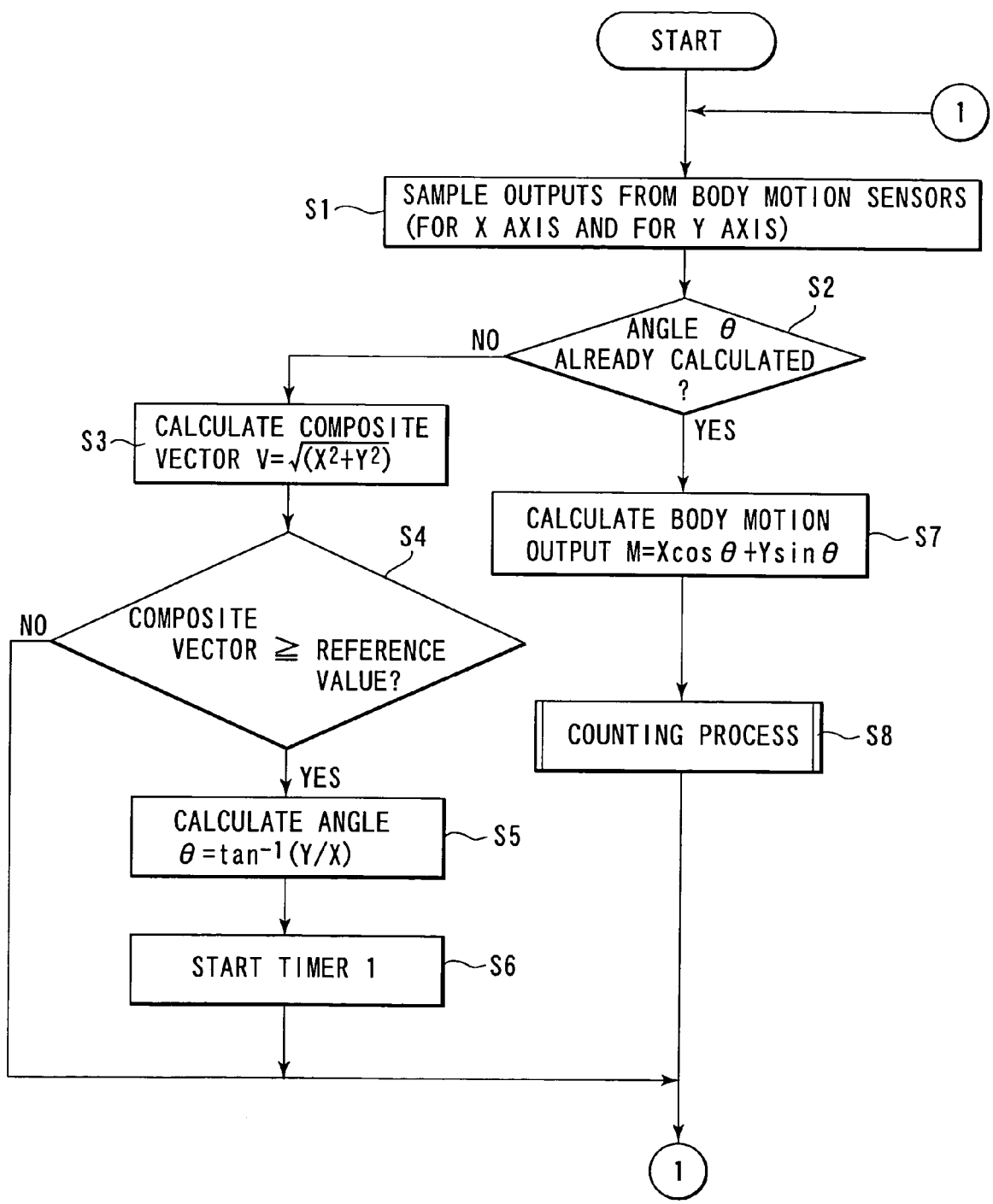
FIG. 3 is a main flowchart showing the flow of primary operations of the body motion measuring apparatus (Example 1).

Next, the operation of the body motion measuring apparatus as Example 1 will be described by use of a main flowchart in FIG. 3 for illustrating the flow of primary operations of the body motion measuring apparatus, a subroutine flowchart in FIG. 4 for illustrating the flow of operations in a counting process, a diagram in FIG. 5 for illustrating the relationship between the inclination and output of the body motion measuring apparatus, and waveform charts in FIG. 6 for illustrating output relationships when the body motion measuring apparatus is inclined.

Firstly, the flow of main operations of the body motion measuring apparatus will be described by use of the main flowchart of FIG. 3. Firstly, when a user attaches the body motion measuring apparatus to a belt, a pocket or the like and operates the input unit 2 so as to start a measurement, body motions are detected by the body motion sensors 4 (4a for the X axis and 4b for the Y axis) at a time, and the outputs are amplified by the amplifiers 5 and 6 and then digitized by the AD converters 7 and 8. The digitized outputs are then sampled by the CPU 10 (STEP S1).

Then, the CPU 10 determines whether an angle θ (corresponding to $θ_1$ in FIG. 5B, $θ_2$ in FIG. 5C, $θ_3$ in FIG. 5D or the like) when the ratio between the magnitude X of an output based on the body motion sensor (for the X axis) 4a and the magnitude Y of an output based on the body motion sensor (for the Y axis) 4b, i.e., the magnitudes X and Y of motions in directions perpendicular to each other, is represented by a tangent is already calculated (STEP S2).

Then, if the angle θ is not yet calculated (NO in STEP S2), the CPU 10 (composite vector calculation means) calculates the size V of a composite vector of the magnitudes X and Y of the motions in the directions perpendicular to each other by use of the above formula (1) (STEP S3).

Then, the CPU 10 (composite vector determination means) compares the calculated size V of the composite vector with a reference value (value to determine a body motion output) so as to determine whether the size V is not smaller than the reference value (STEP S4).

Then, if the size V of the composite vector is smaller than the reference value (NO in STEP S4), the CPU 10 returns to STEP S1 and performs the sampling and subsequent processes again. Meanwhile, if the size V of the composite vector is not smaller than the reference value (YES in STEP S4), the CPU 10 (angle calculation means) calculates the angle θ when the ratio between the magnitudes X and Y of the motions in the directions perpendicular to each other is represented by a tangent by use of the above formula (2) (STEP S5).

Then, in the CPU 10 (body motion counting means), a timer 1 in the CPU 10 is started (STEP S6).

Meanwhile, if the angle θ is already calculated (YES in STEP S2), the CPU 10 (body motion output calculation means) calculates a body motion output M by use of the above formula (3) (STEP S7).

Then, the CPU 10 (body motion counting means) performs a counting process with respect to the calculated body motion output M (STEP S8) and then returns to STEP S1 and performs the sampling and subsequent processes again.

Secondly, the flow of operations in the counting process will be described by use of the subroutine flowchart of FIG. 4. Firstly, the CPU 10 (body motion counting means) compares the body motion output M calculated by the body motion output calculation means (STEP S7) with an upper limit (value to determine that a body motion is to be counted as a predetermined body motion; shown by an Su line in FIGS. 6D and 6G) so as to determine whether the body motion output M is larger than the upper limit (STEP S21).

Then, if the body motion output M is not larger than the upper limit (NO in STEP S21), the CPU 10 compares elapsed time 1, i.e., time elapsed since the start (or reset) of the timer 1, with reference time 1 (time to determine that a body motion is to be counted as the predetermined body motion) so as to determine whether the elapsed time 1 is not longer than the reference time 1 (STEP S22).

Then, if the elapsed time 1 is not longer than the reference time 1 (YES in STEP S22), the CPU 10 returns to STEP S1 and performs the sampling and subsequent processes again. Meanwhile, if the elapsed time 1 is longer than the reference time 1 (NO in STEP S22), the already calculated angle θ is canceled (STEP S23).

Then, the CPU 10 stops and resets the timer 1 (STEP S24) and then returns to STEP S1 and performs the sampling and subsequent processes again.

Meanwhile, if the body motion output M is larger than the upper limit (YES in STEP S21), the body motion is counted as the predetermined body motion (step) (STEP S25).

Then, the CPU 10 waits for a predetermined time period (time period to determine that a body motion is to be counted as the next predetermined body motion) (STEP S26).

Then, the CPU 10 resets the timer 1 (STEP S27) and then returns to STEP S1 and performs the sampling and subsequent processes again.

As described above, the body motion measuring apparatus as Example 1 detects the magnitudes of motions in X and Y directions perpendicular to each other at a time by the body motion sensors, calculates the size V of a composite vector by the composite vector calculation means, compares the size V of the composite vector with a reference value which determines a body motion output so as to determine whether the size V is not smaller than the reference value by the composite vector determination means, calculates an angle θ where the ratio between the magnitudes Y and X of the motions in the directions perpendicular to each other is represented by a tangent by the angle calculation means, calculates a body motion output M taking the angle θ into account by the body motion output calculation means, and counts a predetermined body motion by the body motion counting means.

Figure 5A:
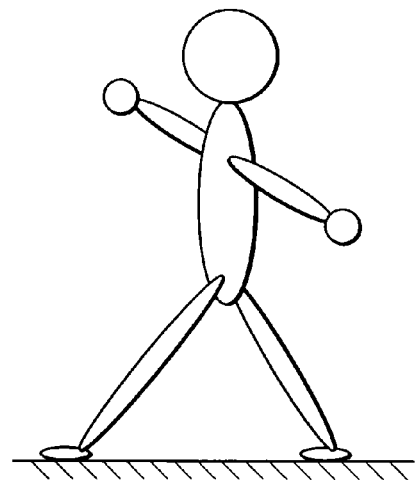
FIG. 5 is a diagram for illustrating the relationship between the inclination and output of the body motion measuring apparatus, wherein 5A shows a user who makes a predetermined body motion (motion by walking), 5B shows the relationship between outputs from body motion sensors and a body motion output when the body motion measuring apparatus is held in a normal position, 5C shows the relationship between outputs from the body motion sensors and a body motion output when the body motion measuring apparatus is held at 45° from its normal position, and 5D shows the relationship between outputs from the body motion sensors and a body motion output when the body motion measuring apparatus is held at 90° from its normal position (Example 1).
Figure 5B:
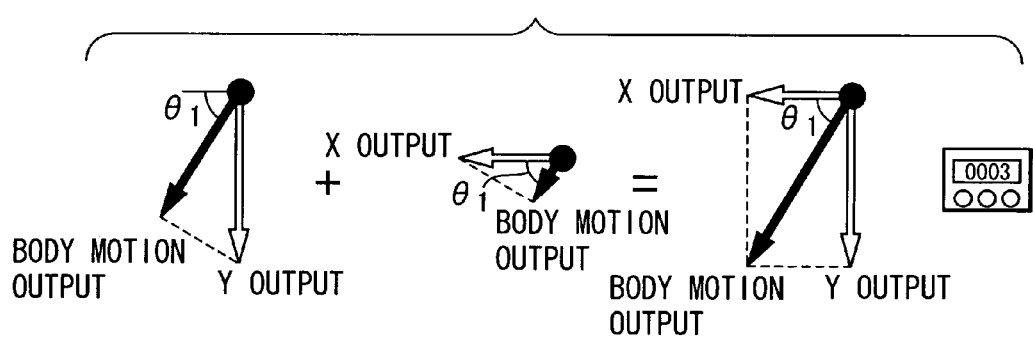
Figure 5C:
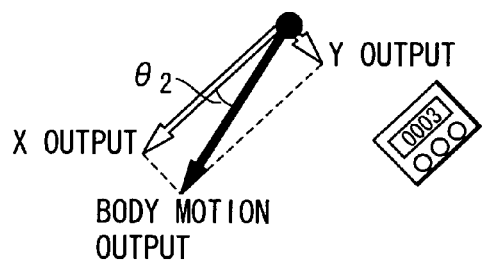
Figure 5D:
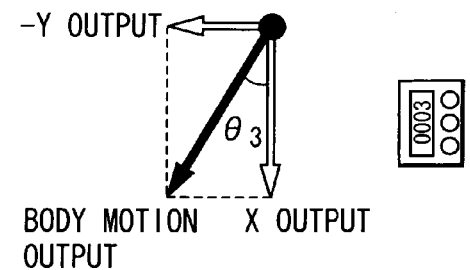
Figure 6A:
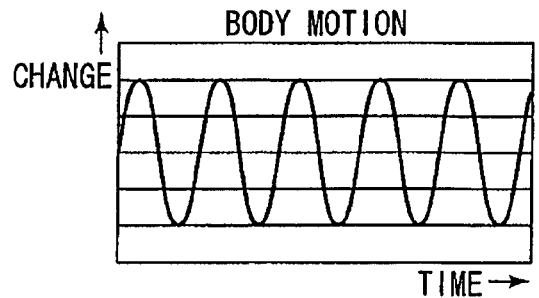
FIG. 6 is waveform charts for illustrating output relationships when the body motion measuring apparatus is inclined, wherein 6A shows a waveform by a predetermined body motion (motion by walking), 6B shows the waveform of an output X from a body motion sensor (for an X axis) when the body motion measuring apparatus is held at 45° from its normal position, 6C shows the waveform of an output Y from a body motion sensor (for a Y axis) when the body motion measuring apparatus is held at 45° from its normal position, 6D shows the waveform of a body motion output when the body motion measuring apparatus is held at 45° from its normal position, 6E shows the waveform of an output X from the body motion sensor (for the X axis) when the body motion measuring apparatus is held at 90° from its normal position, 6F shows the waveform of an output Y from the body motion sensor (for the Y axis) when the body motion measuring apparatus is held at 90° from its normal position, and 6G shows the waveform of a body motion output when the body motion measuring apparatus is held at 90° from its normal position (Example 1).
Figure 6B:
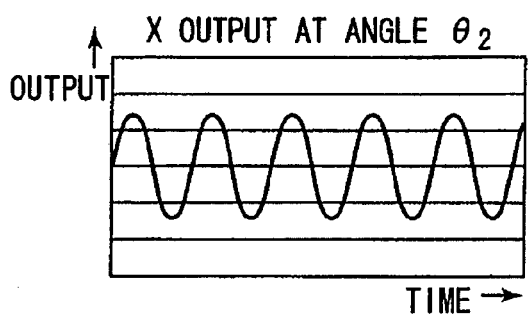
Figure 6E:
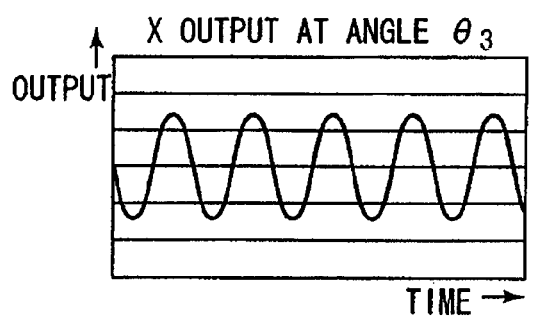
Figure 6C:
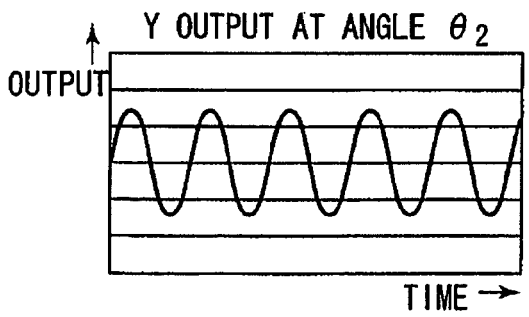
Figure 6F:
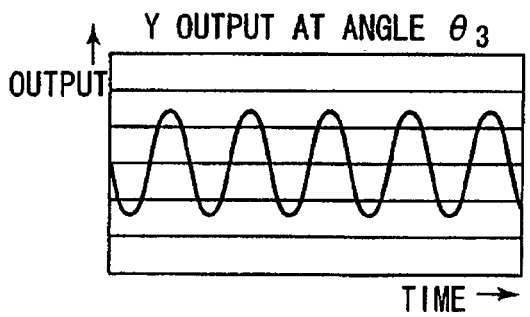
Figure 6D:
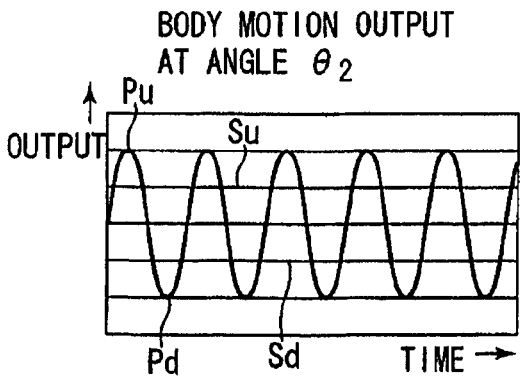
Figure 6G:
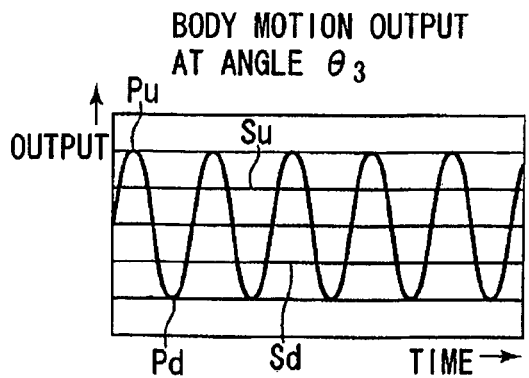
Figure 7:
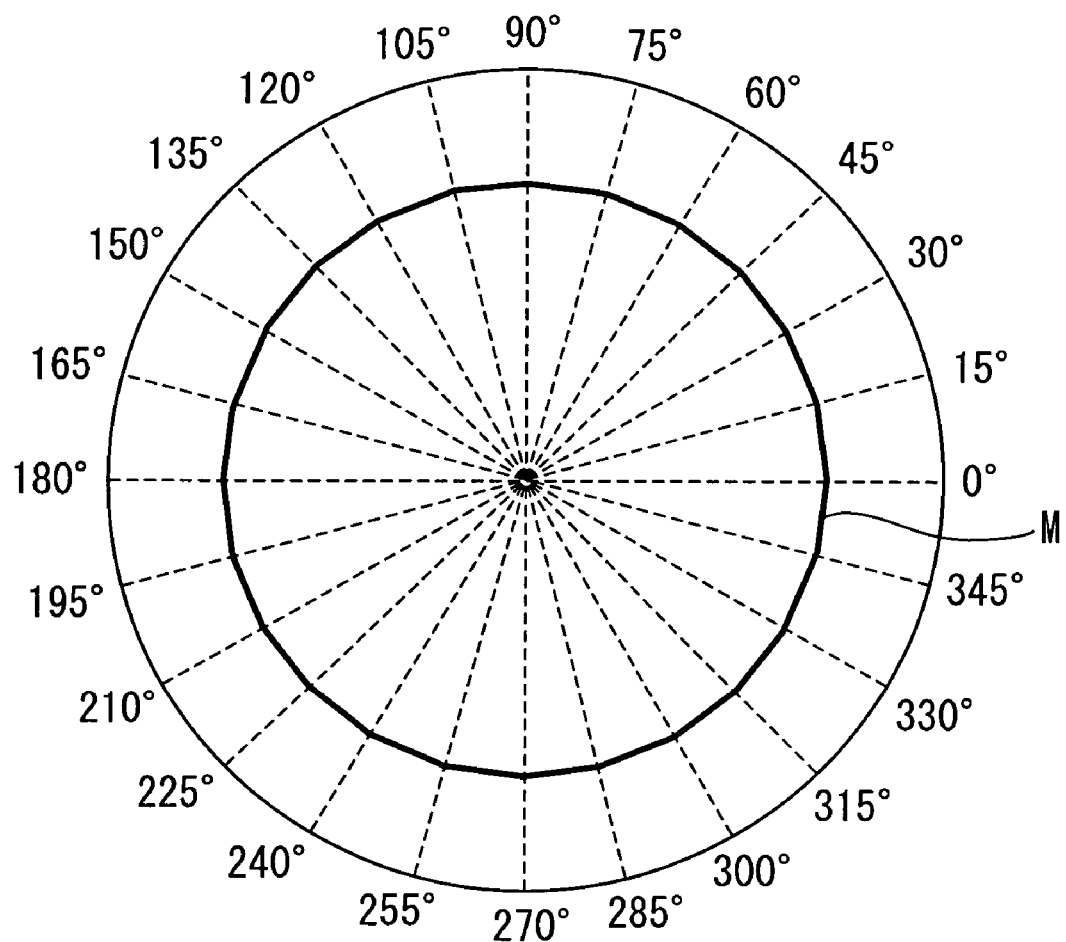
FIG. 7 is a graph showing the relationship between angles at which the body motion measuring apparatus is inclined and a body motion output (Example 1).

Thus, when a state that a user who makes predetermined body motions (motions by waking) as shown in FIG. 5A carries the body motion measuring apparatus in a position as shown in FIG. 5B is assumed to be a normal state and when the body motion measuring apparatus is inclined as shown in FIG. 5C and the magnitudes X and Y of motions in directions perpendicular to each other become outputs as shown in FIGS. 6B and 6C or when the body motion measuring apparatus is inclined as shown in FIG. 5D and the magnitudes X and Y of motions in the directions perpendicular to each other become outputs as shown in FIGS. 6E and 6F, the same body motion output can still be obtained as shown in FIG. 6D or 6G, as long as the body motion of the user remains the same. Further, as shown in FIG. 7, the same (nearly equal-sized) body motion output can be obtained regardless of what angle the body motion measuring apparatus is inclined at. FIG. 7 is a graph whose radial direction represents body motion outputs and circumferential direction represents angles at which the body motion measuring apparatus is inclined.

EXAMPLE 2

Firstly, the constitution of a body motion measuring apparatus (embodiment for preventing the influence of measurement error by inclination in three axial directions) as Example 2 will be described by use of a perspective view of the body motion measuring apparatus in FIG. 8 and a block diagram in FIG. 9 for illustrating the constitution of the body motion measuring apparatus.

The body motion measuring apparatus as Example 2 has an input unit 2 and a display unit 3 on the front face of chassis 1 and also has an electronic substrate 11 inside the chassis 1. The electronic substrate 11 comprises body motion sensors 4 (4a for an X axis, 4b for a Y axis and 4c for a Z axis), amplifiers 5, 6 and 12, AD converters 7, 8 and 13, a storage unit 9 and a CPU 10. These components roughly constitute the whole apparatus.

The input unit 2 takes inputs for starting measurements, switching, setting/registration, and the like. The display unit 3 displays an input status, measurement results, and the like. The storage unit 9 stores various data.

Figure 8:
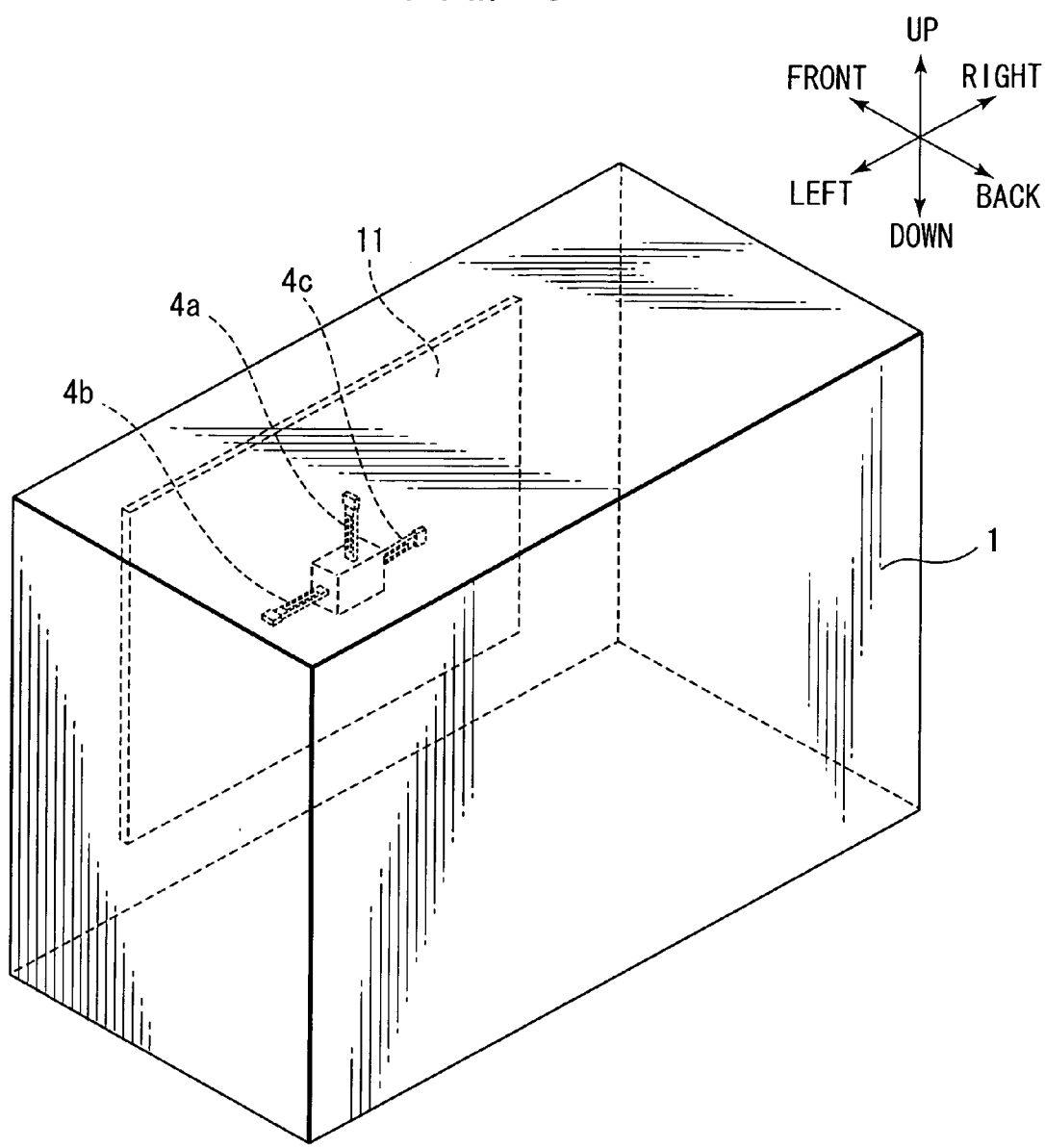
FIG. 8 is a perspective view of a body motion measuring apparatus (Example 2).
Figure 9:
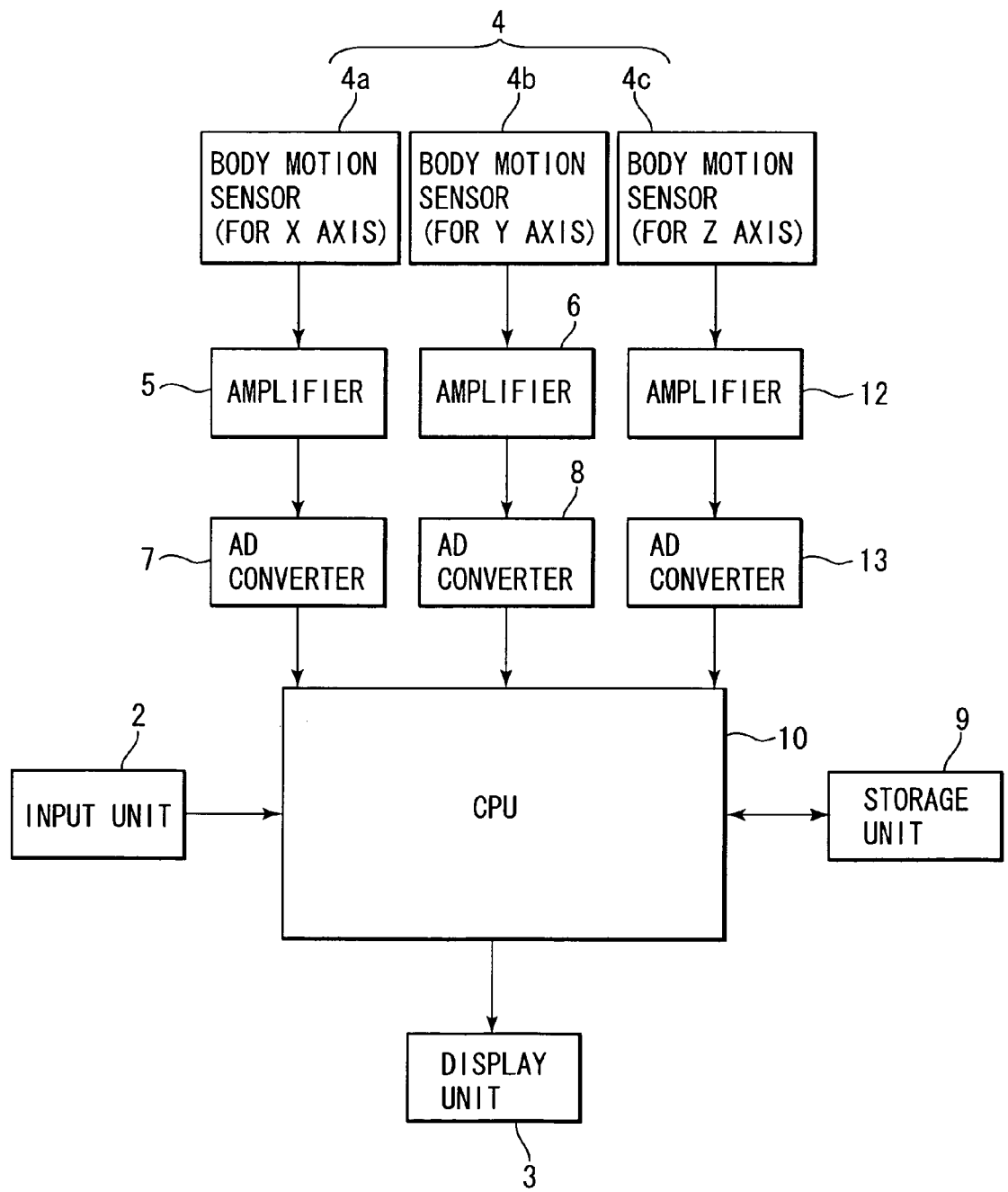
FIG. 9 is a block diagram showing the constitution of the body motion measuring apparatus (Example 2).

The body motion sensor (for the X axis) 4a detects the magnitude of a motion of the chassis 1 in its left or right direction, when the direction of the chassis 1 is defined as shown in FIG. 8 with respect to the directions (front, back, up, down, left and right). The body motion sensor (for the Y axis) 4b detects the magnitude of a motion of the chassis 1 in its up or down direction, when the direction of the chassis 1 is defined as shown in FIG. 8 with respect to the directions (front, back, up, down, left and right). The body motion sensor (for the Z axis) 4c detects the magnitude of a motion of the chassis 1 in its front or back direction, when the direction of the chassis 1 is defined as shown in FIG. 8 with respect to the directions (front, back, up, down, left and right). The body motion sensor (for the X axis) 4a, the body motion sensor (for the Y axis) 4b and the body motion sensor (for the Z axis) 4c detect body motions at a time (simultaneously).

The amplifier 5 amplifies an output (analog) from the body motion sensor (for the X axis) 4a. The amplifier 6 amplifies an output from the body motion sensor (for the Y axis) 4b. The amplifier 12 amplifies an output (analog) from the body motion sensor (for the Z axis) 4c. The AD converter 7 digitizes an output (analog) from the amplifier 5. The AD converter 8 digitizes an output (analog) from the amplifier 6. The AD converter 13 digitizes an output (analog) from the amplifier 12.

The CPU 10 comprises composite vector calculation means, composite vector determination means, angle calculation means, body motion output calculation means and body motion counting means and calculates various data.

The composite vector calculation means calculates a composite vector derived based on the relationship among the magnitude of a motion in the direction detected by the body motion sensor (for the X axis) 4a, the magnitude of a motion in the direction detected by the body motion sensor (for the Y axis) 4b and the magnitude of a motion in the direction detected by the body motion sensor (for the Z axis) 4c. More specifically, the composite vector calculation means calculates the size V of a composite vector by substituting an output X from the AD converter 7 based on the body motion sensor (for the X axis) 4a, an output Y from the AD converter 8 based on the body motion sensor (for the Y axis) 4b and an output Z from the AD converter 13 based on the body motion sensor (for the Z axis) 4c into the following formula (4).

$$V=\sqrt{(X^2+Y^2+Z^2)} \quad (4)$$

The composite vector determination means determines whether the size of the composite vector calculated by the composite vector calculation means is adequate or not. More specifically, the composite vector determination means compares the size of the composite vector calculated by the composite vector calculation means with a reference value so as to determine whether the size of the vector is not smaller than the reference value. The reference value is a value representing a size which can be a candidate for the size of a composite vector by a predetermined body motion.

The angle calculation means calculates an angle derived based on the relationship between the magnitude of the motion in the direction detected by the body motion sensor (for the X axis) 4a and the magnitude of the motion in the direction detected by the body motion sensor (for the Y axis) 4b, when the size of the composite vector determined by the composite vector determination means is adequate. More specifically, the angle calculation means calculates an angle $\theta_{XY}$ by substituting the output X from the AD converter 7 based on the body motion sensor (for the X axis) 4a and the output Y from the AD converter 8 based on the body motion sensor (for the Y axis) 4b into the following formula (5).

$$\theta_{XY}=\tan^{-1}(Y/X) \quad (5)$$

In addition, the angle calculation means also calculates an angle $\theta_{BZ}$ by substituting the output Z from the AD converter 13 based on the body motion sensor (for the Z axis) 4c and a body motion output B based on the magnitudes X and Y of motions in directions perpendicular to each other which is calculated by the body motion output calculation means to be described later into the following formula (6).

$$\theta_{BZ}=\tan^{-1}(Z/B) \quad (6)$$

The body motion output calculation means calculates a body motion output derived based on the relationships between the magnitudes X, Y and Z of the motions in the directions detected by the body motion sensor (for the X axis) 4a, the body motion sensor (for the Y axis) 4b and the body motion sensor (for the Z axis) 4c and the angles calculated by the angle calculation means. More specifically, the body motion output calculation means calculates a body motion output B based on the magnitudes Y and X of the motions in the directions perpendicular to each other by substituting the output X from the AD converter 7 based on the body motion sensor (for the X axis) 4a, the output Y from the AD converter 8 based on the body motion sensor (for the Y axis) 4b and the angle $\theta_{XY}$ calculated by the angle calculation means into the following formula (7).

$$B=X\cos\theta_{XY}+Y\sin\theta_{XY} \quad (7)$$

In addition, the body motion output calculation means also calculates a body motion output M based on the magnitudes X, Y and Z of the motions in the directions perpendicular to one another by substituting the output Z from the AD converter 13 based on the body motion sensor (for the Z axis) 4c, the above calculated body motion output B and the angle $\theta_{BZ}$ calculated by the angle calculation means into the following formula (8).

$$M=B\cos\theta_{BZ}+Z\sin\theta_{BZ} \quad (8)$$

The body motion counting means times predetermined elapsed time and counts a predetermined motion based on the relationship between the body motion output calculated by the body motion output calculation means and the predetermined elapsed time. More specifically, the body motion counting means compares the body motion output calculated by the body motion output calculation means with an upper limit so as to determine whether the body motion output is larger than the upper limit. When the body motion output is larger than the upper limit, the body motion counting means counts it as the predetermined body motion, while when the body motion output is not larger than the upper limit, the body motion counting means executes processing corresponding to the elapsed time.

Figure 10:
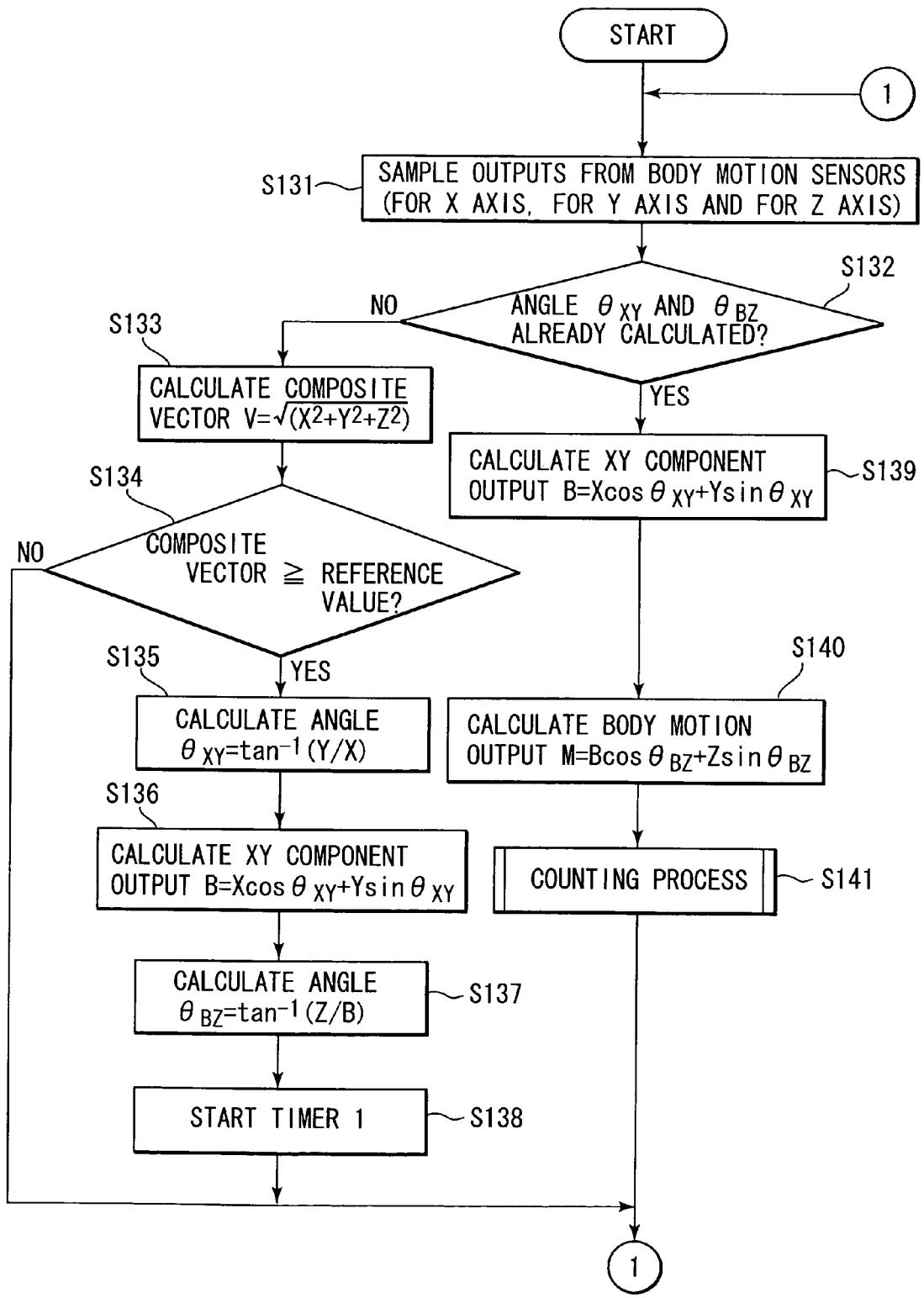
FIG. 10 is a main flowchart showing the flow of primary operations of the body motion measuring apparatus (Example 2).

Next, the operation of the body motion measuring apparatus as Example 2 will be described by use of a main flowchart in FIG. 10 for illustrating the flow of primary operations of the body motion measuring apparatus.

Firstly, when a user attaches the body motion measuring apparatus to a belt, a pocket or the like and operates the input unit 2 so as to start a measurement, body motions are detected by the body motion sensors 4 (4a for the X axis, 4b for the Y axis and 4c for the Z axis) at a time, and the outputs are amplified by the amplifiers 5, 6 and 12 and then digitized by the AD converters 7, 8 and 13. The digitized outputs are then sampled by the CPU 10 (STEP S131).

Then, the CPU 10 determines whether an angle $\theta_{XY}$ when the ratio between Y and X is represented by a tangent and an angle $\theta_{BZ}$ when the ratio between the composition of X and Y and Z is represented by a tangent are already calculated (STEP S132), wherein X, Y and Z represent the magnitudes of outputs based on the body motion sensor (for the X axis) 4a, the body motion sensor (for the Y axis) 4b and the body motion sensor (for the Z axis) 4c, i.e., the magnitudes of motions in directions perpendicular to one other.

Then, if the angles $\theta_{XY}$ and $\theta_{BZ}$ are not yet calculated (NO in STEP S132), the CPU 10 (composite vector calculation means) calculates the size V of a composite vector of the magnitudes X, Y and Z of the motions in the directions perpendicular to one another by use of the above formula (4) (STEP S133).

Then, the CPU 10 (composite vector determination means) compares the calculated size V of the composite vector with a reference value (value to determine a body motion output) so as to determine whether the size V is not smaller than the reference value (STEP S134).

Then, if the size V of the composite vector is smaller than the reference value (NO in STEP S134), the CPU 10 returns to STEP S131 and performs the sampling and subsequent processes again. Meanwhile, if the size V of the composite vector is not smaller than the reference value (YES in STEP S134), the CPU 10 (angle calculation means) calculates the angle $\theta_{XY}$ when the ratio between the magnitudes Y and X of the motions in the directions perpendicular to each other is represented by a tangent by use of the above formula (5) (STEP S135).

Then, the CPU 10 (body motion output calculation means) calculates a body motion output B by use of the above formula (7) (STEP S136).

Then, the CPU 10 (angle calculation means) calculates the angle $\theta_{BZ}$ when the ratio between the composition of X and Y and Z is represented by a tangent by use of the above formula (6) (STEP S137).

Then, in the CPU 10 (body motion counting means), a timer 1 in the CPU 10 is started (STEP S138).

Meanwhile, if the angles $\theta_{XY}$ and $\theta_{BZ}$ are already calculated (YES in STEP S132), the CPU 10 (body motion output calculation means) calculates a body motion output B by use of the above formula (7) (STEP S139).

Then, the CPU 10 (body motion output calculation means) calculates a body motion output M by use of the above formula (8) (STEP S140).

Then, the CPU 10 (body motion counting means) performs a counting process with respect to the calculated body motion output M (STEP S141) and then returns to STEP S131 and performs the sampling and subsequent processes again.

Figure 4:
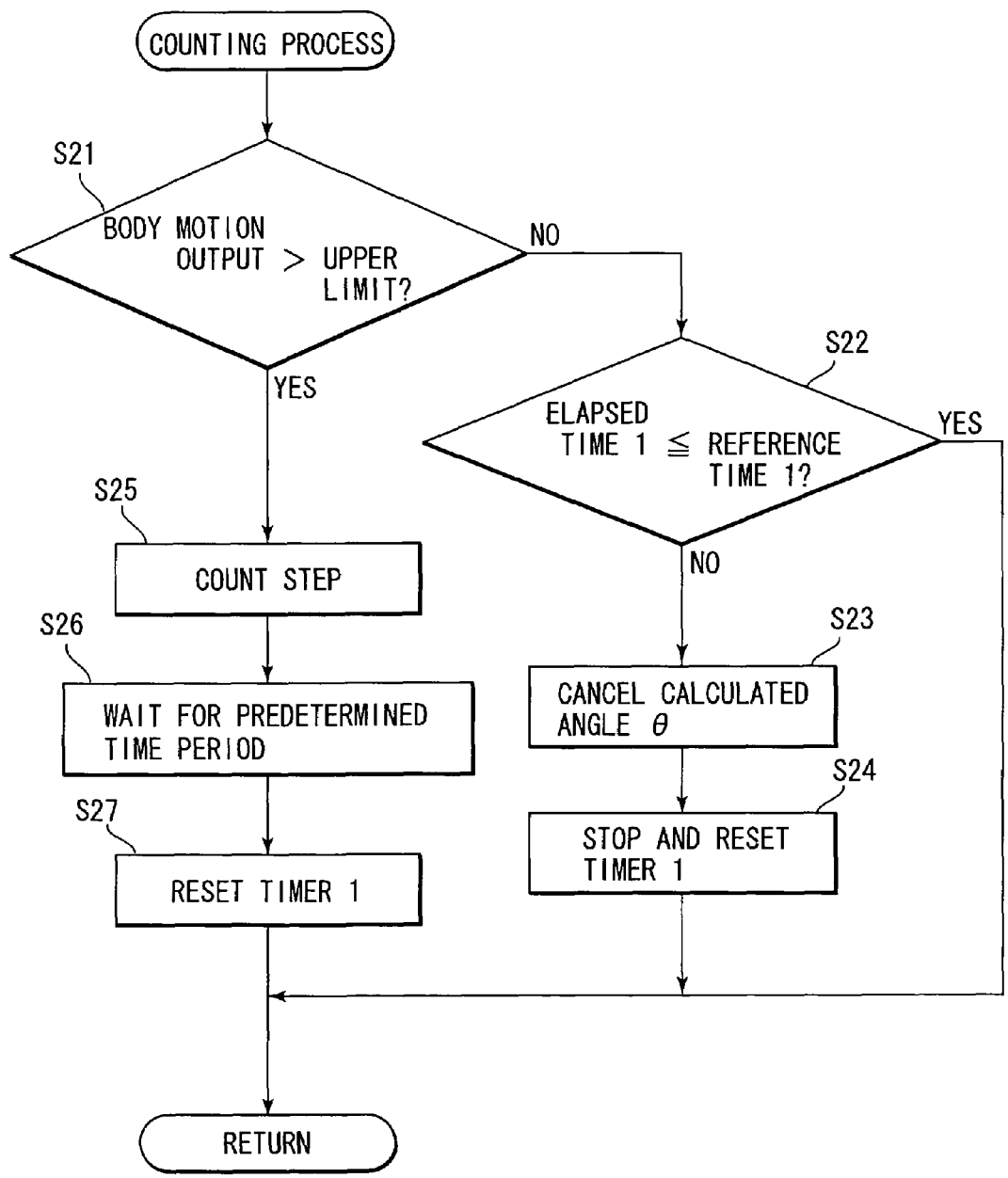
FIG. 4 is a subroutine flowchart showing the flow of operations in a counting process (Example 1).

Operations in the counting process are the same as described in detail by use of FIG. 4 in Example 1.

As described above, the body motion measuring apparatus as Example 2 detects the magnitudes of motions in X, Y and Z directions perpendicular to one other at a time by the body motion sensors, calculates the size V of a composite vector by the composite vector calculation means, compares the size V of the composite vector with a reference value which determines a body motion output so as to determine whether the size V is not smaller than the reference value by the composite vector determination means, calculates an angle $\theta_{XY}$ when the ratio between the magnitudes Y and X of the motions in the directions perpendicular to each other is represented by a tangent and an angle $\theta_{BZ}$ when the ratio between the composition of X and Y and Z is represented by a tangent by the angle calculation means, calculates a body motion output B taking the angle $\theta_{XY}$ into account and based on the magnitudes X and Y of the motions in the directions perpendicular to each other and a body motion output M taking the angle $\theta_{BZ}$ into account and based on the magnitudes X, Y and Z of the motions in the directions perpendicular to one other by the body motion output calculation means, and counts a predetermined body motion by the body motion counting means.

Thus, even if a user who makes predetermined body motions (motions by walking) changes a direction in which he carries the body motion measuring apparatus and the body motion measuring apparatus is inclined at any angle, the same body motion output can be obtained, as long as the body motion of the user remains the same.

Further, in the counting process (FIG. 4) by the body motion counting means in Examples 1 and 2, a body motion is counted as the predetermined body motion when a body motion output calculated by the body motion output calculation means is larger than the upper limit. However, it is also possible to carry out processes as shown by the flow of operations in a counting process by subroutine flowcharts in FIG. 11, 12 or 13, and 14. Next, these processes will be described.

Figure 11:
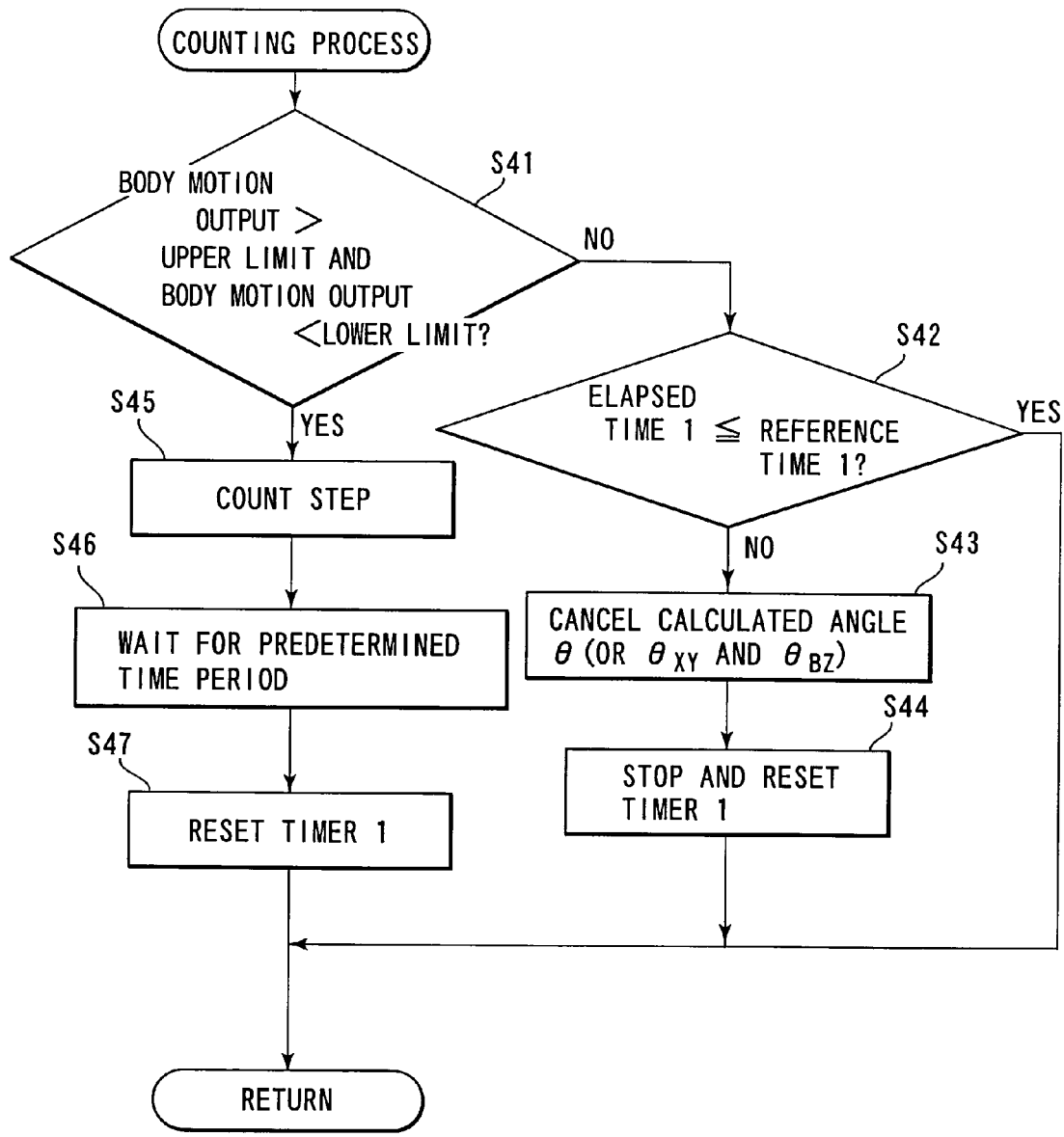
FIG. 11 is a subroutine flowchart showing the flow of operations in another exemplary counting process.

The flow of operations in the counting process according to the subroutine flowchart of FIG. 11 will be described. Firstly, the CPU 10 (body motion counting means) compares the body motion output M calculated by the body motion output calculation means (STEP S7 or STEP S140) with an upper limit (value to determine that a body motion is to be counted as the predetermined body motion; shown by an Su line in FIGS. 6D and 6G in the case of Example 1) and a lower limit (value to determine that a body motion is to be counted as the predetermined body motion; shown by an Sd line in FIGS. 6D and 6G in the case of Example 1) so as to determine whether the body motion output M is larger than the upper limit and lower than the lower limit (STEP S41). Detailed descriptions of the following subsequent STEPS S42 to S47 will be omitted because they are similar to STEPS S22 to S27 in FIG. 4. Thus, the body motion may be counted as the predetermined body motion when the body motion output calculated by the body motion output calculation means is larger than the upper limit and lower than the lower limit.

Figure 12:
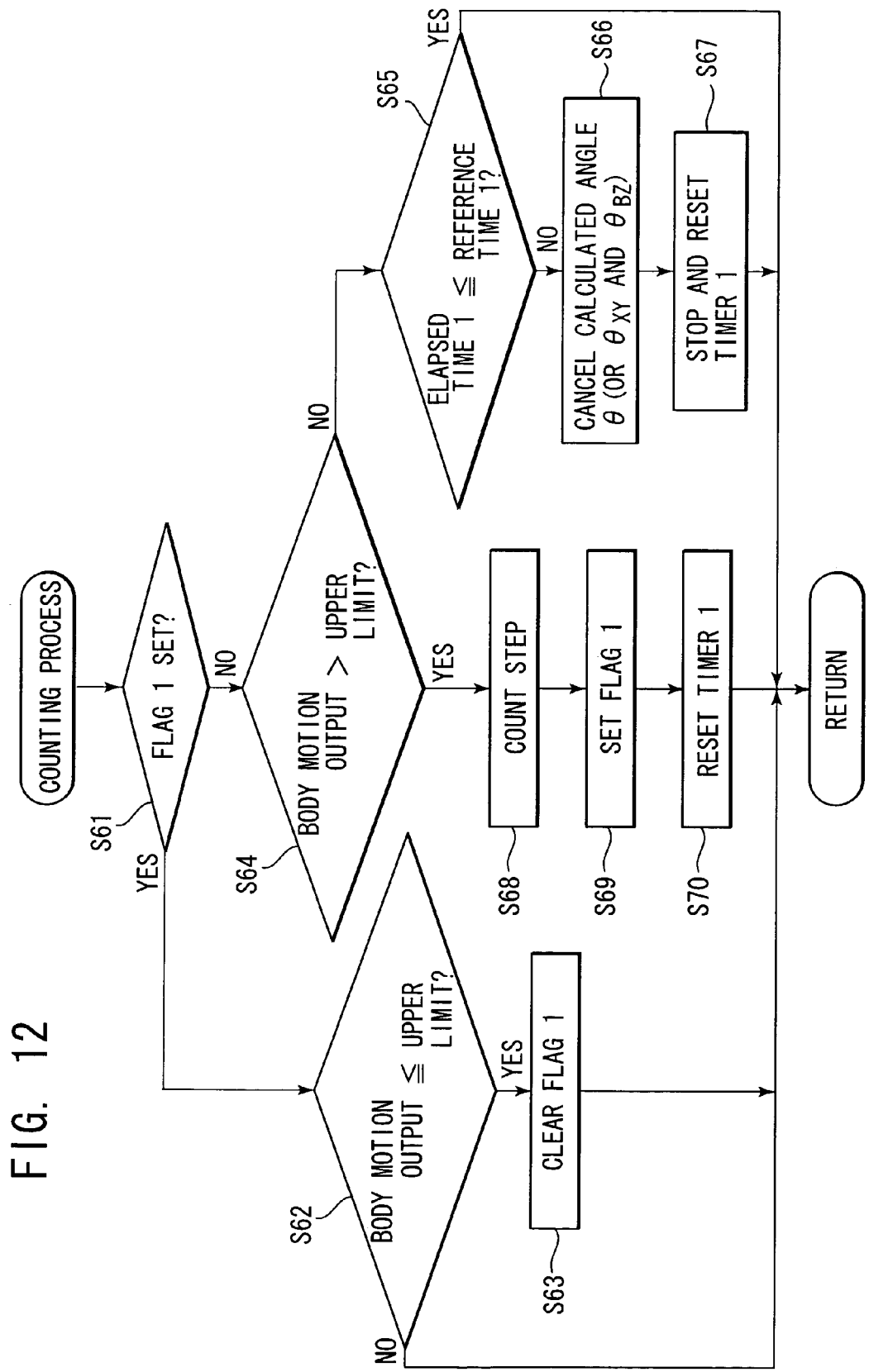
FIG. 12 is a subroutine flowchart showing the flow of operations in another exemplary counting process.

Next, the flow of operations in the counting process according to the subroutine flowchart of FIG. 12 will be described. Firstly, the CPU 10 (body motion counting means) determines whether a flag 1 is set (STEP S61).

Then, if the flag 1 is set (YES in STEP S61), the CPU 10 compares the body motion output M calculated by the body motion output calculation means (STEP S7 or STEP S140) with an upper limit (value to determine that a body motion is to be counted as the predetermined body motion; shown by the Su line in FIGS. 6D and 6G in the case of Example 1) to determine whether the body motion output M is not larger than the upper limit (STEP S62).

Then, if the body motion output M is larger than the upper limit (NO in STEP S62), the CPU 10 returns to STEP S1 and performs the sampling and subsequent processes again. Meanwhile, if the body motion output M is not larger than the upper limit (YES in STEP S62), the CPU 10 clears the flag 1 (STEP S63).

Then, if the flag 1 is not set (NO in STEP S61), the CPU 10 compares the body motion output M calculated by the body motion output calculation means (STEP S7) with the upper limit (value to determine that a body motion is to be counted as the predetermined body motion; shown by the Su line in FIGS. 6D and 6G in the case of Example 1) so as to determine whether the body motion output M is larger than the upper limit (STEP S64).

Then, if the body motion output M is not larger than the upper limit (NO in STEP S64), the CPU 10 compares elapsed time 1, i.e., time elapsed since the start (or reset) of the timer 1, with reference time 1 (time to determine that a body motion is to be counted as the predetermined body motion) so as to determine whether the elapsed time 1 is not longer than the reference time 1 (STEP S65).

Then, if the elapsed time 1 is not longer than the reference time 1 (YES in STEP S65), the CPU 10 returns to STEP S1 and performs the sampling and subsequent processes again. Meanwhile, if the elapsed time 1 is longer than the reference time 1 (NO in STEP S65), the already calculated angle θ (or $\theta_{XY}$ and $\theta_{BZ}$) are canceled (STEP S66).

Then, the CPU 10 stops and resets the timer 1 (STEP S67) and then returns to STEP S1 and performs the sampling and subsequent processes again.

Meanwhile, if the body motion output M is larger than the upper limit (YES in STEP S64), the body motion is counted as the predetermined body motion (step) (STEP S68).

Then, the CPU 10 sets the flag 1 (STEP S69), resets the timer 1 (STEP S70), and then returns to STEP S1 or STEP S131 and performs the sampling and subsequent processes again.

Figure 13:
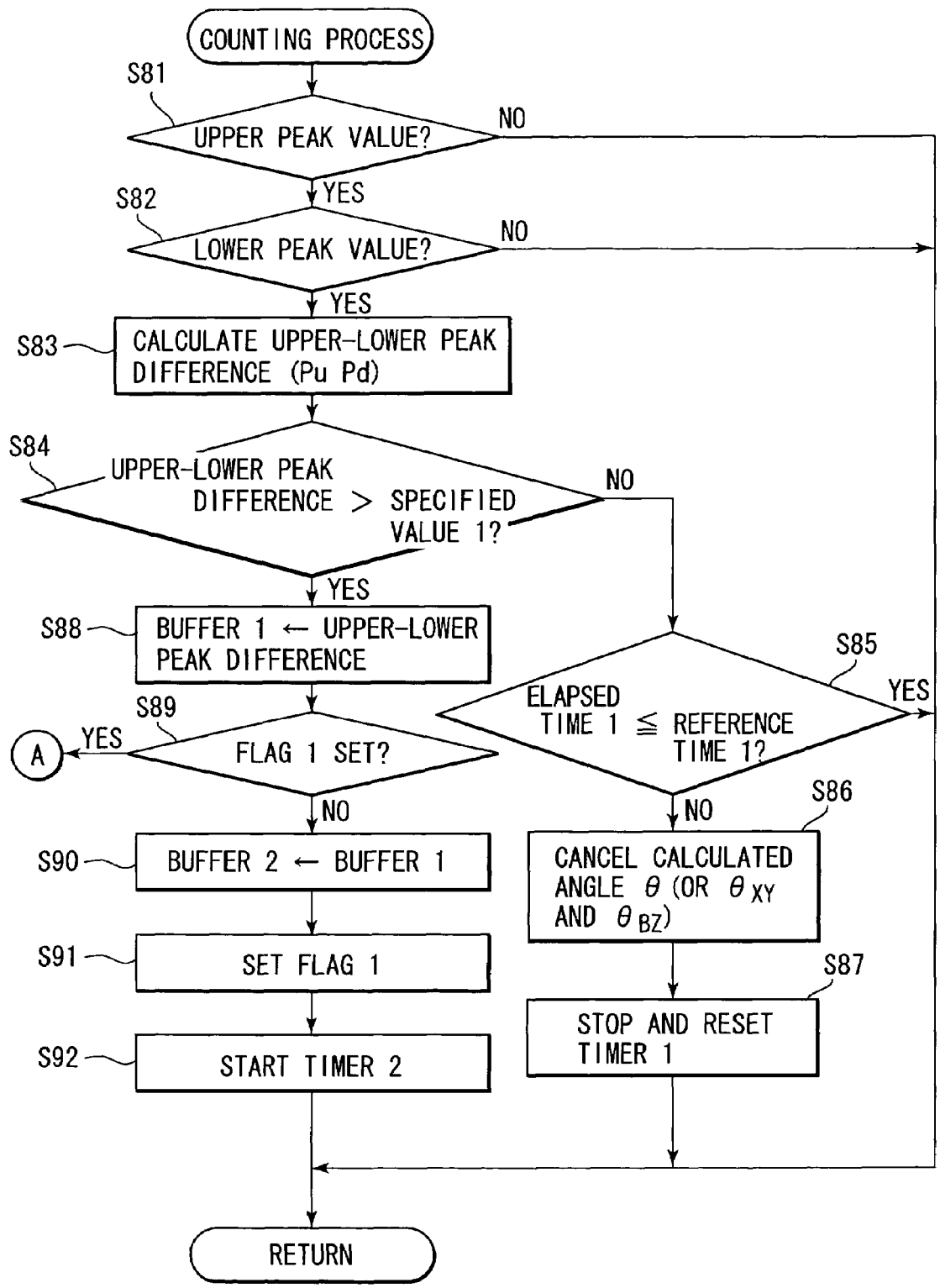
FIG. 13 is a subroutine flowchart showing the flow of operations in another exemplary counting process.
Figure 14:
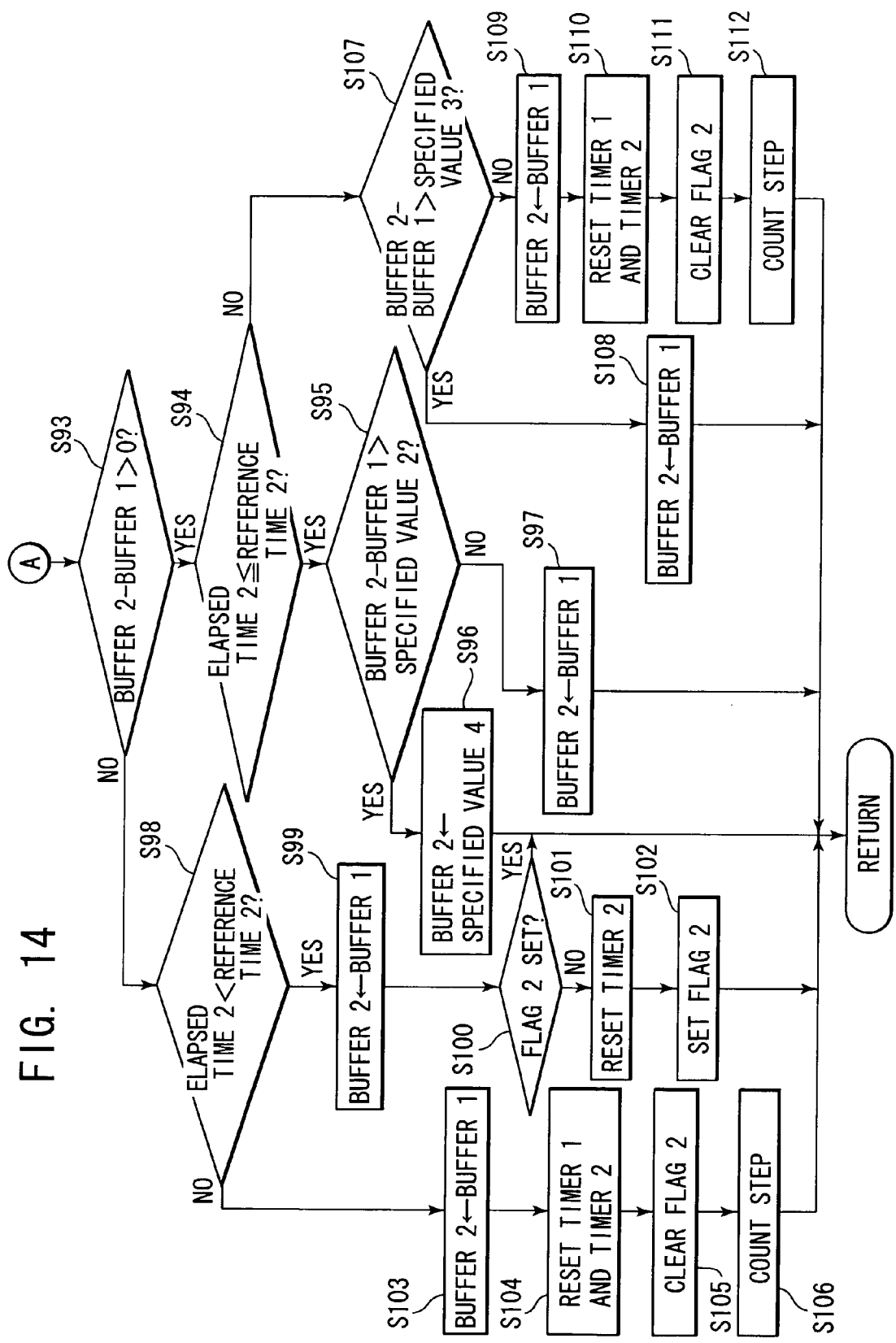
FIG. 14 is a subroutine flowchart showing the flow of operations in another exemplary counting process.
Figure 15:
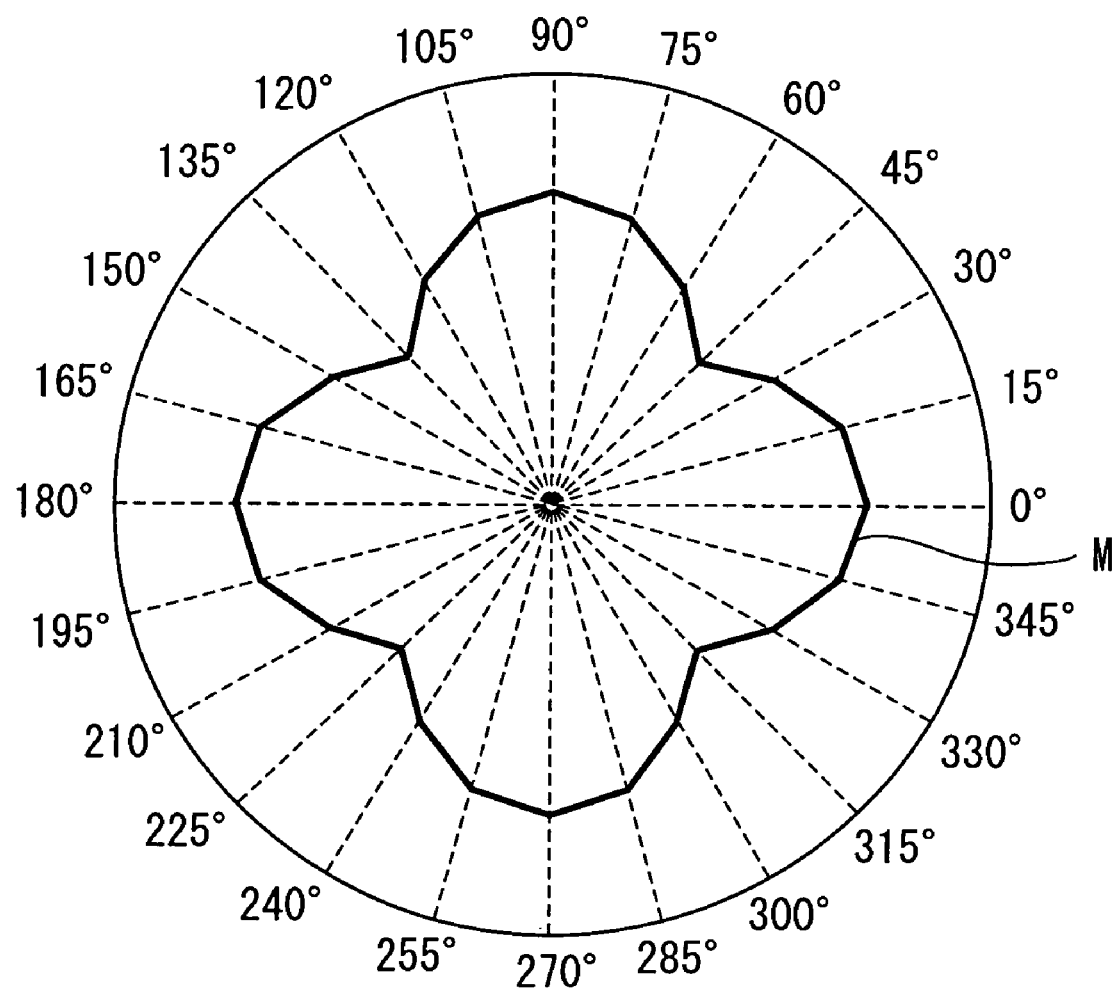
FIG. 15 is a graph showing the relationship between angles at which the body motion measuring apparatus is inclined and a body motion output (Background Art).

Next, the flow of operations in the counting process according to the subroutine flowchart of FIG. 13 will be described. Firstly, the CPU 10 (body motion counting means) determines whether the body motion output M calculated by the body motion output calculation means (STEP S7 or STEP S140) corresponds to an upper peak value (Pu point in FIGS. 6D and 6G in the case of Example 1) (STEP S81).

Then, if the body motion output M does not correspond to the upper peak value (NO in STEP S81), the CPU 10 returns to STEP S1 and performs the sampling and subsequent processes again. Meanwhile, if the body motion output M corresponds to the upper peak value (YES in STEP S81), the CPU 10 determines whether the body motion output M corresponds to a lower peak value (Pd point in FIGS. 6D and 6G in the case of Example 1) (STEP S82).

Then, if the body motion output M does not correspond to the lower peak value (NO in STEP S82), the CPU 10 returns to STEP S1 and performs the sampling and subsequent processes again. Meanwhile, if the body motion output M corresponds to the lower peak value (YES in STEP S82), the CPU 10 calculates an upper-lower peak difference which represents the difference between the upper peak value and the lower peak value (STEP S83).

Then, the CPU 10 compares the calculated upper-lower peak difference with a specified value 1 (value to determine that a body motion is to be counted as the predetermined body motion) so as to determine whether the difference is larger than the specified value 1 (STEP S84).

Then, if the upper-lower peak difference is not larger than the specified value 1 (NO in STEP S84), the CPU 10 compares elapsed time 1, i.e., time elapsed since the start (or reset) of the timer 1, with reference time 1 (time to determine that a body motion is to be counted as the predetermined body motion) so as to determine whether the elapsed time 1 is not longer than the reference time 1 (STEP S85).

Then, if the elapsed time 1 is not longer than the reference time 1 (YES in STEP S85), the CPU 10 returns to STEP S1 and performs the sampling and subsequent processes again. Meanwhile, if the elapsed time 1 is longer than the reference time 1 (NO in STEP S85), the already calculated angle θ (or $\theta_{XY}$ and $\theta_{BZ}$) is canceled (STEP S86).

Then, the CPU 10 stops and resets the timer 1 (STEP S87) and returns to STEP S1 or STEP S131 and performs the sampling and subsequent processes again.

Meanwhile, if the upper-lower peak difference is larger than the specified value 1 (YES in STEP S84), the CPU 10 substitutes the upper-lower peak difference into a buffer 1 (STEP S88) and determines whether the flag 1 is set (STEP S89).

Then, if the flag 1 is not set (NO in STEP S89), the CPU 10 substitutes the upper-lower peak difference stored in the buffer 1 into a buffer 2 (STEP S90).

Then, the CPU 10 sets the flag 1 (STEP S91), starts a timer 2 (STEP S92), and then returns to STEP S1 or STEP S131 and performs the sampling and subsequent processes again.

Meanwhile, if the flag 1 is set (YES in STEP S89), the CPU 10 calculates a peak difference between the upper-lower peak difference stored in the buffer 2 and the upper-lower-peak difference stored in the buffer 1 and determines whether the calculated peak difference is larger than 0 (STEP S93).

Then, if the peak difference is larger than 0 (YES in STEP S93), the CPU 10 compares elapsed time 2, i.e., time elapsed since the start (or reset) of the timer 2, with reference time 2 so as to determine whether the elapsed time 2 is not longer than the reference time 2 (STEP S94).

Then, if the elapsed time 2 is not longer than the reference time 2 (YES in STEP S94), the CPU 2 compares the peak difference with a specified value 2 so as to determine whether the peak difference is larger than the specified value 2 (STEP S95).

Then, if the peak difference is larger than the specified value 2 (YES in STEP S95), the CPU 10 substitutes a specified value 4 into the buffer 2 (STEP S96) and then returns to STEP S1 and performs the sampling and subsequent processes again. Meanwhile, if the upper-lower peak difference is not larger than the specified value 2 (NO in STEP S95), the CPU 10 substitutes the upper-lower peak difference stored in the buffer 1 into the buffer 2 (STEP S97) and then returns to STEP S1 or STEP S131 and performs the sampling and subsequent processes again.

Meanwhile, if the elapsed time 2 is longer than the reference time 2 (NO in STEP S94), the CPU 10 compares the upper-lower peak difference with a specified value 3 so as to determine whether the upper-lower peak difference is larger than the specified value 3 (STEP S107).

Then, if the peak difference is larger than the specified value 3 (YES in STEP S107), the CPU 10 substitutes the upper-lower peak difference stored in the buffer 1 into the buffer 2 (STEP S108) and then returns to STEP S1 or STEP S131 and performs the sampling and subsequent processes again.

Meanwhile, if the peak difference is not larger than the specified value 3 (value to determine that a body motion is not to be counted as the predetermined body motion) (NO in STEP S107), the CPU 10 substitutes the upper-lower peak difference stored in the buffer 1 into the buffer 2 (STEP S109), resets the timer 1 and the timer 2 (STEP S110), clears the flag 2 (STEP S111), counts the body motion as the predetermined body motion (step) (STEP S112), and returns to STEP S1 or STEP S131 and performs the sampling and subsequent processes again.

Meanwhile, if the peak difference is not larger than 0 (NO in STEP S93), the CPU 10 compares the elapsed time 2 with the reference time 2 so as to determine whether the elapsed time 2 is not longer than the reference time 2 (STEP S98).

Then, if the elapsed time 2 is not longer than the reference time 2 (YES in STEP S99), the CPU 10 substitutes the upper-lower peak difference stored in the buffer 1 into the buffer 2 (STEP S99) and determines whether the flag 2 is set (STEP S100).

Then, if the flag 2 is set (YES in STEP S100), the CPU 10 returns to STEP S1 or STEP S131 and performs the sampling and subsequent processes again. Meanwhile, if the flag 2 is not set (NO in STEP S100), the CPU 10 resets the timer 2 (STEP S101), sets the flag 2 (STEP S102), and then returns to STEP S1 or STEP S131 and performs the sampling and subsequent processes again.

Meanwhile, if the elapsed time 2 is longer than the reference time 2 (NO in STEP S98), the CPU 10 substitutes the upper-lower peak difference stored in the buffer 1 into the buffer 2 (STEP S103), resets the timer 1 and the timer 2 (STEP S104), clears the flag 2 (STEP S105), counts the body motion as the predetermined body motion (step) (STEP S106), and then returns to STEP S1 or STEP S131 and performs the sampling and subsequent processes again.

What is claimed is:

1. A body motion measuring apparatus comprising:
   body motion sensors,
   composite vector calculation means,
   composite vector determination means,
   angle calculation means,
   body motion output calculation means, and
   body motion counting means,
   wherein
   the body motion sensors detect the magnitudes of motions in different directions at a time,
   the composite vector calculation means calculates the size of a composite vector derived based on the relationship between the magnitudes of the motions in the directions detected by the body motion sensors,
   the composite vector determination means determines the adequacy of the size of the composite vector calculated by the composite vector calculation means,
   the angle calculation means calculates an angle derived based on the relationship between the magnitudes of the motions in the directions detected by the body motion sensors, when the size of the composite vector determined by the composite vector determination means is adequate,
   the body motion output calculation means calculates a body motion output derived from the relationship between the magnitudes of the motions in the directions detected by the body motion sensors and the angle by the angle calculation means, and
   the body motion counting means times predetermined elapsed time and counts a predetermined body motion based on the relationship between the body motion output calculated by the body motion output calculation means and the predetermined elapsed time.

2. The apparatus of claim 1, wherein
   the body motion sensors detect the magnitudes X and Y of motions in X and Y directions perpendicular to each other at a time, the composite vector calculation means calculates the size V of a composite vector by substituting the magnitudes X and Y of the motions in the directions perpendicular to each other into a formula represented by $V=\sqrt{(X^2+Y^2)}$,
   the composite vector determination means compares the size V of the composite vector calculated by the composite vector calculation means with a reference value to determine whether the size V is not smaller than the reference value,
   the angle calculation means calculates an angle θ by substituting the magnitudes X and Y of the motions in the directions perpendicular to each other detected at a time by the body motion sensors into a formula represented by $\theta=\tan^{-1}(Y/X)$, and
   the body motion output calculation means calculates a body motion output M by substituting the magnitudes X and Y of the motions in the directions perpendicular to each other detected at a time by the body motion sensors and the angle θ calculated by the angle calculation means into a formula represented by $M=X\cos\theta+Y\sin\theta$.

3. The apparatus of claim 1, wherein
   the body motion sensors detect the magnitudes X, Y and Z of motions in X, Y and Z directions perpendicular to one another at a time,
   the composite vector calculation means calculates the size V of a composite vector by substituting the magnitudes X, Y and Z of the motions in the directions perpendicular to one another detected at a time by the body motion sensors into a formula represented by $V=\sqrt{(X^2+Y^2+Z^2)}$,
   the composite vector determination means compares the size V of the composite vector calculated by the composite vector calculation means with a reference value to determine whether the size V is not smaller than the reference value,
   the angle calculation means calculates an angle $\theta_{XY}$ by substituting the magnitudes X and Y of the motions in the directions perpendicular to each other detected at a time by the body motion sensors into a formula represented by $\theta_{XY}=\tan^{-1}(Y/X)$,
   the body motion output calculation means calculates a body motion output B based on the magnitudes Y and X of the motions in the directions perpendicular to each other, by substituting X and Y out of the magnitudes of the motions in the directions perpendicular to one another detected at a time by the body motion sensors and the angle $\theta_{XY}$ calculated by the angle calculation means into a formula represented by $B=X\cos\theta_{XY}+Y\sin\theta_{XY}$,
   the angle calculation means also calculates an angle $\theta_{BZ}$ by substituting Z out of the magnitudes of the motions in the directions perpendicular to one another detected at a time by the body motion sensors and the body motion output B calculated by the body motion output calculation means into a formula represented by $\theta_{BZ}=\tan^{-1}(Z/B)$, and
   the body motion output calculation means also calculates a body motion output M based on the magnitudes X, Y and Z of the motions in the directions perpendicular to one another, by substituting the calculated body motion output B, Z out of the magnitudes of the motions in the directions perpendicular to one another detected at a time by the body motion sensors, and the angle $\theta_{BZ}$ calculated by the angle calculation means into a formula represented by $M=B\cos\theta_{BZ}+Z\sin\theta_{BZ}$.

4. The apparatus of claim 1, wherein the body motion counting means counts the body motion as the predetermined body motion when the body motion output M calculated by the body motion output calculation means is larger than an upper limit.

5. The apparatus of claim 2, wherein the body motion counting means counts the body motion as the predetermined body motion when the body motion output M calculated by the body motion output calculation means is larger than an upper limit.

6. The apparatus of claim 3, wherein the body motion counting means counts the body motion as the predetermined body motion when the body motion output M calculated by the body motion output calculation means is larger than an upper limit.

7. The apparatus of claim 1, wherein the body motion counting means counts the body motion as the predetermined body motion when the body motion output M calculated by the body motion output calculation means is larger than an upper limit and lower than a lower limit.

8. The apparatus of claim 2, wherein the body motion counting means counts the body motion as the predetermined body motion when the body motion output M calculated by the body motion output calculation means is larger than an upper limit and lower than a lower limit.

9. The apparatus of claim 3, wherein the body motion counting means counts the body motion as the predetermined body motion when the body motion output M calculated by the body motion output calculation means is larger than an upper limit and lower than a lower limit.

10. The apparatus of claim 1, wherein the body motion counting means counts the body motion as the predetermined body motion based on the relationship between the state of change in difference between the upper peak and lower peak of the body motion output M calculated by the body motion output calculation means and the predetermined elapsed time.

11. The apparatus of claim 2, wherein the body motion counting means counts the body motion as the predetermined body motion based on the relationship between the state of change in difference between the upper peak and lower peak of the body motion output M calculated by the body motion output calculation means and the predetermined elapsed time.

12. The apparatus of claim 3, wherein the body motion counting means counts the body motion as the predetermined body motion based on the relationship between the state of change in difference between the upper peak and lower peak of the body motion output M calculated by the body motion output calculation means and the predetermined elapsed time.

* * * * *